United States Patent [19]

Sterling

[11] 4,019,504
[45] Apr. 26, 1977

[54] MEDICAL SPLINT KIT

[76] Inventor: Robert E. Sterling, 210 Brom Bones Lane, Longwood, Fla. 32750

[22] Filed: May 7, 1975

[21] Appl. No.: 575,577

[52] U.S. Cl. .......................... 128/88; 128/DIG. 15
[51] Int. Cl.² ......................................... A61F 5/04
[58] Field of Search ................ 128/87 R, 89 R, 90, 128/DIG. 15, 88

[56] References Cited

UNITED STATES PATENTS

| | | | |
|---|---|---|---|
| 2,947,306 | 8/1960 | Culkin | 128/87 R |
| 3,027,336 | 3/1962 | Gotz et al. | 128/90 X |
| 3,358,141 | 12/1967 | Hoffmann et al. | 128/DIG. 15 |
| 3,469,268 | 9/1969 | Phillips | 128/87 R |
| 3,640,273 | 2/1972 | Ray | 128/87 |
| 3,719,187 | 3/1973 | Ulansey | 128/90 |

OTHER PUBLICATIONS

Tru Loc, Rocford Safety Eqpt. Co. p. 92.
Jobst–Jet, Emergency Medical Products Division p. 91.

*Primary Examiner*—Lawrence W. Trapp
*Attorney, Agent, or Firm*—Eugene F. Friedman

[57] ABSTRACT

A medical splint kit having reusable components and serviceable during the X-raying of the body part involved. The kit has a splint member formed from a material transparent to X-irradiation such as an acrylic plastic. The splint also includes sections of minute loops or hooks to facilitate its affixation to the body member. Straps having hooks or loops, respectively, which will engage the sections on the splint affix the splint to the body. By incorporating sections of both hooks and loops, the strap, after surrounding the body member, will adhere to itself and retain the splint adjacent to and supportive of the injured area. A second splint member may also form part of the kit. A locking device passing through slots in both members hold the members together and provide an adjustable splint that can conform to the particular body member involved. Non-skid surfaces on both splint members will aid the splint in retaining their respective configuration. The kit allows the application of the splint on a single side of a body extremity and its continued use through the X-raying of that portion.

13 Claims, 6 Drawing Figures

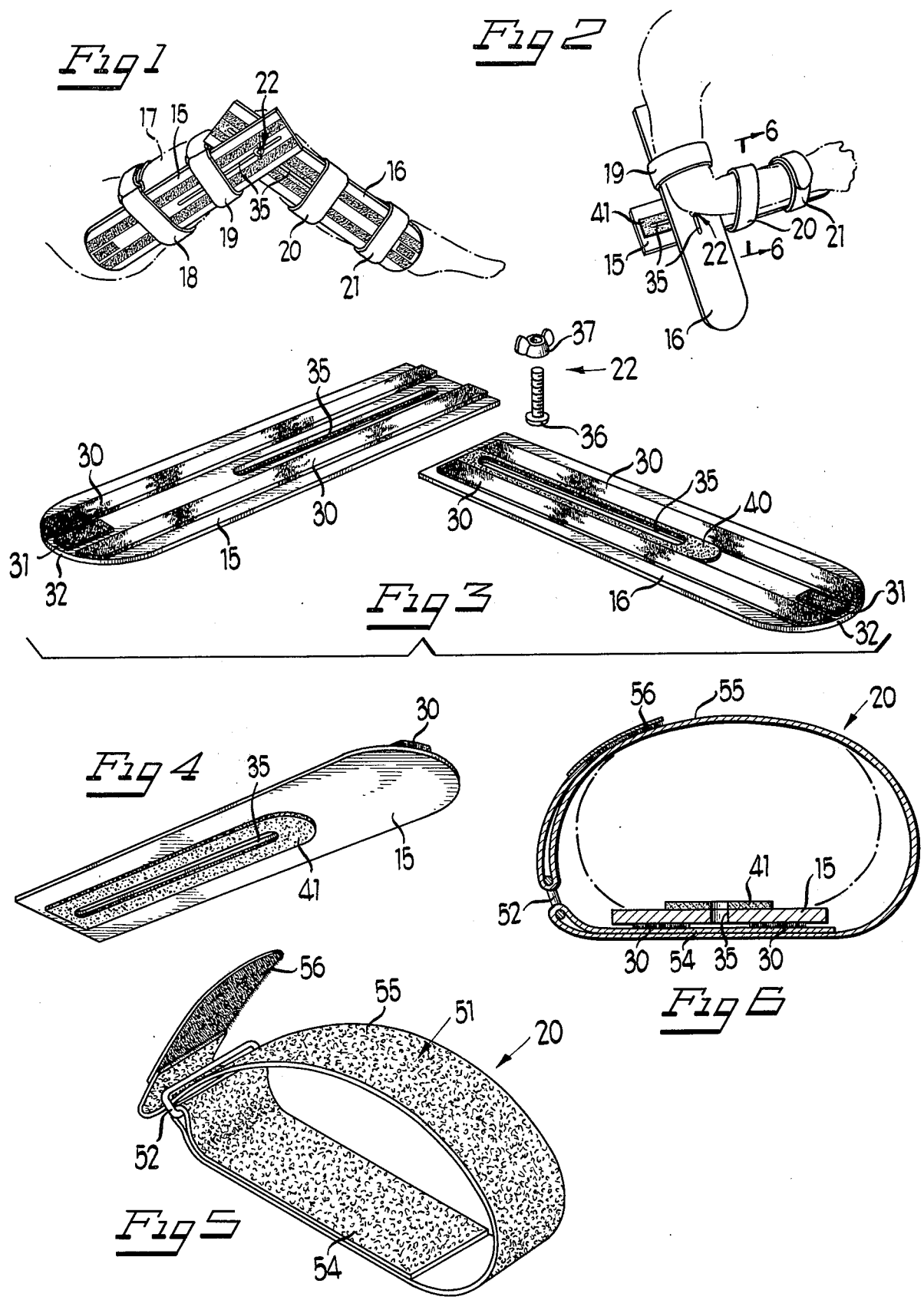

MEDICAL SPLINT KIT

BACKGROUND

Medical splints find use in supporting a body member, generally an extremity, which has incurred a fracture in its skeletal structure. The splint immobilizes the portion of the body involved in order to minimize the patient's suffering and the aggravation of the injury produced by relative motion of the skeletal structures involved.

Classically, splinting a fractured extremity involved placing wood slats on both sides of the injured portion and bandaging it and the slats with extensive amounts of tape, cloth or other wrapping material. This technique necessitated extensive handling and movement of the injured structure and the subsequent production of the deleterious results supposedly avoided through the use of a splint. Further, opacity of the splint to X-irradiation precluded its use during that type of examination. Moreover, removing the splint again involved substantial manipulation of the structure involved.

One company, in a product marketed by it, has modified the classical splint by adding a second rigid slat for each side of the body member involved. The two slats on each side have a slot running down their middles through which a locking device passes. This arrangement allows the slats to assume an angular configuration approximating that of an injured appendage such as an arm or leg. When locked in position, the usual wrapping procedure then affixes the slat to the limb. This procedure, however, still displays the disadvantages of the classical splint discussed above. The extensive wrapping may aggravate the pain and injury while the X-ray opaque material for the splint precludes its use during diagnosis.

To avoid extensive wrapping, U.S. Pat. No. 3,640,273 to T. D. Ray discloses various straps for attaching the splint to the appendage. These straps may consist of one or two pieces. They have a configuration which allows them to tightly circumscribe the splint prior to application upon a person's limb. Sections of hooks and loops, such as those bearing the Velcro trademark, allow the ends of the strap to attach to themselves after affixing the splint to the limb.

However, the straps lack positive attachment to the splint. Consequently, it may move up or down the splint and inadequately immoblize the involved body portion.

J. T. Ulansey, in his U.S Pat. No. 3,719,187, shows a flexible splint which attempts to ameliorate this problem by including openings in the splint for a strap. The dimensions of the openings limit the longitudinal motion of the strap along the splint. However, this arrangement requires the placement of the strap at the site of openings. This may not represent the preferred location for the straps in every instance. To make the apparatus operate properly for a fracture, Ulansey suggests the use of adhesive tape. That, of course, entails subjecting injured portion to appreciable motion.

Moreover, the size of the openings permits the straps to pass freely through them. This could result in the splint moving about the limb. Precluding this motion requires tightening the strap on the injured portion.

Accordingly, notwithstanding these developments, the search continues for an improved splint arrangement. Desirably, it should facilitate its use in emergency conditions with a minimum of pain and aggravation of the injury. In doing so, the splint should provide a wide latitude of choices for the exact location and arrangement of the straps for different body members, different sizes of the body members, and different locations of fractures or other injuries within the member.

SUMMARY

Including a holding means which affixes the straps positively to the splint avoids many of the problems discussed above and allows greater utility of the splint itself. The holding means should include two parts, one of which connects to the splint and the other to the straps.

The splint generally has the form of a substantially rigid elongated member. A web affixes the splint or elongated member adjacent to a body member. The holding device results in the positive adherence of the web to the splint in a substantially fixed relationship.

This positive adherence in a fixed relationship obviates extensive handling of the injured portion. Previously, the multiple wraps around an injury attempted to secure the splint to the body in such a fashion that the splint would not move around. The positive adherence between the straps and the splint minimizes or eliminates this motion.

The holding means may take the form of sections of loops and hooks, such as those sold under the Velcro trademark. In this instance, a long section of one type may connect to the splint while the web includes a short section of the other type. This arrangement allows the strap to connect at any portion along the splint. The web may thus connect to the splint at the best location for securing minimal relative motion between the splint and the body rather than at specific sites built into the splint. This of course eliminates the need for additional amounts of adhesive tape to obtain a secure and fixed relationship between the splint and the body.

As suggested above, one part of the holding means may contain a multitude of small hooks while the other part includes the loops. Pressing the two parts together results in their adherence to each other. Separating one part from the other leaves them in a condition that they may reengage each other. Thus, the hooks and loops represent one example of holding means that remains serviceable even after a number of uses. This allows the straps to affix to and remove from the splint a large number of times.

The web itself may assume the form of a strap having sections of both hooks and loops. This not only permits its adherence to the splint, but after wrapping around the injured body portion, it may engage itself to form a closed tight loop surrounding the splint and the body portion.

This web and splint and affix to a body member without extensive manipulation of the injured area. They also permit their facile removal, again without extensive movement of the body. Consequently, they may find use during the X-ray diagnosis of the injured region. Their removal from the injured area does not substantially alter the conditions existing during the X-ray taking. To find use in this situation, the elongated member, or splint, must be substantially transparent to X-irradiation.

BRIEF DESCRIPTION OF THE FIGURES

FIG. 1 shows a splint composed of two members attached to a leg by Velcro straps removably fixed to the splint.

FIG. 2 shows the same splint of FIG. 1 but attached to an arm.

FIG. 3 gives a viw of the two members of the splint in FIGS. 1 and 2.

FIG. 4 gives an underside view of the splint member to the left in FIG. 3.

FIG. 5 shows the construction of one of the straps used in FIGS. 1 and 2 to attach the splint to a body portion.

FIG. 6 gives a cross-sectional view along the line 6—6 of FIG. 2 showing a strap attached to one of the splint members in the configuration it has when affixing the splint to a body extremity.

DETAILED DESCRIPTION

FIG. 1 shows a splint composed of the two members 15 and 16 held to the leg 17 by the four straps 18, 19, 20 and 21. The wing nut 22 retains the two splint members 15 and 16 at a fixed relationship relative to each other.

The same splint members 15 and 16 support the arm 25 in FIG. 2. As a result of the smaller size of the arm as compared to a leg, the three straps 19, 20 and 21 suffice to hold the splint in place.

In FIG. 3, the two splint members 15 and 16 appear separated from each other to illustrate their structure. Each has the form of an elongated member.

For each of the splint members 15 and 16, the surface disposed away from the body carries two strips or sections of minute hooks 30. These generally come in the form of cloth strips and readily adhere to the surfaces of the members 15 and 16 with glue. The straps 18 through 21 have cooperating loops which allow them to affix to the hook strips 30 and, thus, the members 15 and 16. Alternately, strips of loops could reside upon the members 15 and 16 rather than the hooks 30.

Each of the splint members 15 and 16 also have an additional small section of hooks 31 at their rounded ends 32. In conjunction with a long strap containing appropriately placed loops and passing around the neck, the hook section 31 assists in the use of the splint with a sling.

Each of the splint members also possesses an elongated slot 35 running down its middle. This permits the use of the two splint members 15 and 16 together as shown in FIGS. 1 and 2. At times and depending upon the particular injury involved, a single splint member 15 or 16 may suffice by itself. In this instance, of course, the slot 35 becomes unnecessary.

Generally, the bolt 36, preferably a step bolt, passes through the slot 35 on each of the members 15 and 16 with the step, when used, in the slot 35. In order to place the bolt 36, rather than the nut 37, next to the body, the bolt 36 should pass through the member 16 from the bottom first, and then through the member 15. The nut 37 then engages the bolt 36 and tightens down onto the top of the member 15 itself If desired, a fibre glass, phenolic or plastic spacer may separate the nut 37 from the surface of the splint member 15 to preclude marring the latter.

The use of the splint generally involves configuring the splint members 15 and 16 relative to each other to approximate the shape of the injured body portion, as shown in FIGS. 1 and 2. This avoids the necessity of configuring the injured portion to match the splint.

Loosening the nut 37, if not sufficiently loose, allows the two members 15 and 16 to move relative to each other. As illustrated in FIGS. 1 and 2, this relative motion may include a rotation about the wing nut 22 as well as a translation of one or both of the members 15 and 16 relative to each other to achieve the desired length of splint. Tightening the nut 37 then preserves the desired configuration. To prevent slipping, the splint member 16 includes, on its upper surface in FIG. 3, the rubber strip 40 which surrounds the slot 35. Similarly, the splint member 15 includes the rubber strip 41 which surrounds the slot 35 on its bottom surface as FIG. 4 shows. Upon configuring the splint portions to approximate the injured portion of the body, the rubber strips 40 and 41 contact each other. Moreover, since the strips 40 and 41 surround the slots 35, tightening the wing nut combination 22 forces the strips 40 and 41 into intimate contact with each other. Having a higher coefficient of friction than the rest of the splint, the contact between the rubber strips 40 and 41 helps maintain the desired relative configuration.

The strap 20, appearing in FIG. 5, provides a convenient and facile means for holding the splint members 15 and 16 against a body portion. It also allows its painless removal from the injured area with only a minimum of movement of the body.

The strap 20 includes a long section of loops 51 which passes through the metal ring 52 and folds back upon itself. The folded-over end 54 of the section of loops securely attaches to the remainder of the loop section 51 by any such suitable means as glueing or sewing. This arrangement, of course, fastens the ring 52 to the strap 50.

Moreover, in the area possessing the folded-over loop section 51, both sides of the strap 20 possess loops engageable with hooks. This allows end 54 to attach to the hooks 30 connected to the splint members 15 and 16. The loops on the other side at 55 of the strip 20 occupy a position where the hooks at the end 56 of the strap 20, after passing through the ring 52, may engage them to form a band holding the splint to a body extremity.

FIG. 6 gives a cross-section view of the strap 20 on an arm shown in phantom. The splint member 15 has the two rows of hooks 30 extending below itself. These engage the loops on the folded-over section 54. The other end 56 of the strap 20, after surrounding the arm, passes through the ring 52 and folds back upon itself where its hooks at 56 engage the loops at 55 on the outside of the strap 20. With the hooks at 56 engaging the loops at 55, the strap secures the splint member 15 to the arm.

With the configuration shown, disengaging the strap from the injured portion proceeds easily and without disturbance to the body. Thus, in FIG. 6, removal of the strap 20 merely requires lifting the end 56 with the hooks off of the top of the strap with the loops 55 and sliding through the ring 52.

The removal of the strap 20 thus proceeds with no induced motion of the body extremity involved. Consequently, the X-ray diagnosis of the injured area may proceed with the splint attached, since the removal of the straps will not alter the view taken in the X-rays. To allow for this additional use of the splint and the added protection to the injured portion during diagnosis, the splint members 15 and 16 must display substantial transparency to X-irradiation. Constructing them of such material as acrylic plastics will satisfy this criterion.

I claim:

1. An emergency medical-splint kit for application to an injured body portion at the site of an accident comprising:
   a. two substantially rigid elongated members substantially transparent to X-irradiation;
   b. fixing means for retaining said members adjacent to each other and in a substantially fixed relationship, said fixing means permitting changes in the relationship with which said members are affixed to each other;
   c. at least one web of sufficient dimension to wrap around a body portion for affixing said members adjacent to a body portion;
   d. holding means for adhering said web to said elongated members in a substantially fixed relationship, a first part of said holding means being connected to at least one of said elongated members and a second part of said holding means being connected to said web, said holding means allowing said web to be adhered to and removed from said one elongated member a plurality of times; and
   e. joining means forming part of said web means for, with said holding means adhering said web means to said elongated member and with said web means wrapped around said elongated member and a body portion, adjoining together two parts of said web means to affix said member adjacent to a body portion.

2. The kit of claim 1 wherein said holding means permits the adhering of said web to said member with a plurality of different orientations between said web and said member.

3. The kit of claim 2 wherein at least a part of the surface of each of said two elongated members adjacent to the other of said two elongated members has a higher coefficient of friction than the remaining surfaces in order to reduce slippage between said elongated members.

4. The kit of claim 3 wherein said elongated members are constructed of an acrylic plastic.

5. A medical-splint kit comprising:
   a. a substantially rigid elongated member substantially transparent to X-irradiation;
   b. at least one web means for affixing said member adjacent to a body portion;
   c. holding means for adhering said web means to said elongated member in a substantially fixed relationship, a first part of said holding means being connected to said elongated member and a second part of said holding means being connected to said web means, said holding means allowing said web means to be adhered to and removed from said elongated member a plurality of times; and
   d. joining means forming part of said web means for, with said holding means adhering said web means to said elongated member with said elongated member positioned adjacent to said body portion, and with said web means substantially wrapped around said body portion, adjoining together, without moving said body portion or said elongated member, two parts of said web to affix said member adjacent to said body portion.

6. The kit of claim 5 wherein said holding means includes two sections, the first section including a plurality of loops and the second section including a plurality of hooks, said first section and said second section remaining adhered to one another when said hooks engage said loops, one of said sections forming at least a portion of said first part of said holding means and the other of said sections forming at least a portion of said second part of said holding means.

7. The kit of claim 6 wherein said web means includes both hooks and loops such that when said second section on said web means is adhered to said first section on said elongated member, and said web means is wrapped around a body portion, at least a portion of said hooks on said web means engage at least a portion of said loops on said web means to retain said elongated member affixed to said body portion.

8. The method of affixing a medical splint to a body portion which comprises:
   a. adhering with a holding means a web to a substantially rigid elongated member substantially transparent to X-irradiation in a substantially fixed relationship, a first part of said holding means being connected to said elongated member and a second part of said holding means being connected to or forming part of said web;
   b. placing said member with said web adhered in proximity to a body portion;
   c. subsequently substantially placing said web around said portion; and
   d. adjoining together, without substantial movement of said member or said portion, two parts of said web in a fashion to affix said members adjacent to said body portions.

9. The method of claim 8 wherein, with said elongated member being a first elongated member, a second substantially rigid elongated member substantially transparent to X-irradiation is affixed, prior to the affixing of said elongated member adjacent to a body extremity, to said first elongated member in a substantially fixed relationship.

10. The method of claim 9 wherein, with said holding means including two sections and the first of said sections including a plurality of loops and the second of said sections including a plurality of hooks, one of said sections forming at least a portion of said first part of said holding means and the other said sections forming at least a portion of said second part of said holding means, the step of adhering said web to said elongated member is accomplished by engaging said loops with said hooks, and wherein with said web including both a plurality of hooks and a plurality of loops during the affixing of said elongated member to a body extremity, a portion of said loops on said web is engaged with a portion of said hooks on said web.

11. The kit of claim 5 including two substantially rigid elongated members substantially transparent to X-irradiation and fixing means for retaining said members adjacent to each other and in a substantially fixed relationship, said fixing means permitting changes in the relationship with which said members are affixed to each other.

12. The kit of claim 11 wherein at least a part of the surface of each of said two elongated members adjacent to the other of said two elongated members has a higher coefficient of friction than the remaining surfaces in order to reduce slippage between said elongated members.

13. The kit of claim 12 wherein said elongated members are constructed of an acrylic plastic.

* * * * *